United States Patent [19]

Anton et al.

[11] Patent Number: 4,683,203
[45] Date of Patent: Jul. 28, 1987

[54] IMMOBILIZED ENZYMES, PROCESSES FOR PREPARING SAME, AND USE THEREOF

[75] Inventors: Octavian Anton, Brussels; Robert Crichton, Louvain-la-Neuve; Jean-Pierre Lenders, La Hulpe, all of Belgium

[73] Assignee: Redco N.V., Kapelle Op Den Bos, Belgium

[21] Appl. No.: 716,694

[22] Filed: Mar. 27, 1985

[30] Foreign Application Priority Data

Apr. 14, 1984 [DE] Fed. Rep. of Germany ....... 3414232
Oct. 6, 1984 [DE] Fed. Rep. of Germany ....... 3436809

[51] Int. Cl.$^4$ ..................... C12P 19/24; C12N 11/14
[52] U.S. Cl. ........................................ 435/94; 435/176
[58] Field of Search ................................. 435/176, 94

[56] References Cited

U.S. PATENT DOCUMENTS

| | | | |
|---|---|---|---|
| 2,871,200 | 1/1959 | Doumani | 502/218 |
| 3,501,324 | 3/1970 | Kubo | 106/120 |
| 4,304,857 | 12/1981 | Brouillard et al. | 435/94 |
| 4,330,519 | 5/1982 | Takahashi et al. | 423/335 |
| 4,368,303 | 1/1983 | McDaniel | 502/232 X |

OTHER PUBLICATIONS

Laskin editor, Enzymes and Immobilized Cells in Biotechnology, 1985, pp. 98, 99, 106.

*Primary Examiner*—Lionel M. Shapiro
*Attorney, Agent, or Firm*—Wegner & Bretschneider

[57] ABSTRACT

Immobilized enzymes covalently bound to an inorganic carrier by an amino group through a bifunctional spacer have improved properties when the carrier is formed of amorphous, approximately spherical silica particles obtained from synthetic calcium silicate. The silica particles have an average particle size of from 15 to 80 $\mu$m, an apparent particle volume of from 1.3 to 3 cm$^3$/g, and a specific surface area of from 250 to 800 m$^2$/g.

7 Claims, No Drawings

IMMOBOLIZED ENZYMES, PROCESSES FOR PREPARING SAME, AND USE THEREOF

The present invention relates to immobilized enzymes that have been covalently bound to an inorganic carrier via an amino group and a bifunctional spacer, to processes for preparing same and to the use thereof.

BACKGROUND OF THE INVENTION

Immobilized enzymes have gained increasing importance in both the preparative and the analytical fields, since the immobilized enzymes may be used several times and can be more readily separated from the reaction medium. Enzymes can be fixed to various carriers in different ways. Carriers to which the enzymes are bound via covalent bonds have proven to be particularly useful. Various organic polymers and inorganic materials have already been employed. Useful known carrier materials are polysaccharides (Sepharose, Sephadex, starch, etc.), synthetic polymers such as polyacrylamides, phenol-formaldehyde resins, and inorganic materials such as glass, aluminium oxides, and silicates.

A covalent binding of enzymes to a carrier in some cases is effected by a covalent bond to an amino group of the carrier through a bifunctional spacer to an amino group of the enzyme. In the event that the carrier material, due to its nature, does not contain free amino groups at its surface, these are first introduced by means of a chemical reaction. To this end, in the case of inorganic carriers, more specifically silicates, 3-aminopropyl trimethoxysilane (APTS), inter alia, has proven to be useful. The enzymes are coupled to these amino groups by convalent bond(s) via a bifunctional spacer. In addition, [3-(2-aminoethyl)aminopropyl]trimethoxysilane can be used.

In practice, among other substances, glutaraldehyde has proven to be particularly useful as a spacer, as it is capable of reacting with amino groups of the carrier as well as with amino groups of the enzyme.

A drawback inherent to organic carrier materials is the sensitivity thereof to organic solvents and higher temperatures and, in some cases, the high costs as well. In contrast to organic polymers, inorganic carrier materials such as glass, aluminates, and silicates, have only a relatively small reactive surface so that they can only hold a relatively small amount of enzyme and, hence, have to be used in substantially larger amounts.

OBJECT OF THE INVENTION

It is the object of the present invention to improve immobilized enzymes having been covalently bound to an inorganic carrier, the improvements, more specifically, relating to the activity and stability thereof.

DESCRIPTION OF THE INVENTION

Surprisingly it has been found that inorganic carriers which are particularly suitable are the amorphous silica particles according to the German Patent Application No. P 34 14 232, corresponding to U.S. application Ser. No. 716,695 filed concurrently in the name of Octavian Anton, Pierre Jacobs, Georges Poncelet, and Philippe Jacques (Attorney Docket No. CAW-19180). These are amorphous, approximately spherical silica particles obtained by the acidic hydrolysis of an approximately spherical synthetic calcium silicate having a particle size of from 20 to 120 $\mu$m, an average particle size of from 15 to 80 $\mu$m, an apparent particle volume of from 1.3 to 3 $cm^3/g$ and a specific surface area of from 250 to 800 $m^2/g$. The term "apparent particle volume" expressed in $cm^3/g$ is the reciprocal of apparent bulk density (expressed in $g/cm^3$), a well-known expression in powder technology. The apparent particle volume was used for the experiments to compare volumes of given weights of powder. These silica particles have a continuous uniform microgranular structure on the external surface thereof and a structure in the interior thereof, which structure only weakly recalls the original crystal needle structure of the starting materials. These silica particles are very well suited as carriers for catalysts. Surprisingly good results have been achieved when using these silica particles as carriers of covalently bound enzymes. To serve this purpose, free amino groups are first introduced at the surface of the silica particles. As the reagent therefor, more particularly, 3-aminopropyl triethoxysilane (APTS) is suitable. The enzymes are bound to these amino groups by covalent bonds through a bifunctional spacer. As a bifunctional spacer, glutaraldehyde has proved to be very useful. To the pre-activated silica particles having thus been obtained, the enzymes may be covalently bound in a per se known manner. Among the enzymes, cellobiase and glucose-isomerase have so far been the subject of thorough investigations, wherein surprisingly good results were obtained. As further enzymes basically, all enzymes of preparative or analytical interest can be envisaged which can be used in immobilized form with a high activity and a high stability. These include, although they are not limited to penicillinamidase, proteases, glucose-oxidases, lipases, cholesterolesterase, cholesteroloxidase, cyanidhydrolase, chymotrypsin, trypsin, cellulases (endo- and exo-), urease, aminoacid oxydases, creatinase, peroxidase and beta-galactosidase.

A particular advantage of the new enzyme carrier consists in that relatively unpurified enzymes may be employed because of the high capacity to bind protein. Immobilized enzymes are bound to the carrier and exhibit high activity and high stability.

The immobilized enzymes according to the present invention may be used for several different purposes. When cellobiase is employed as the enzyme, then glucose can be prepared from cellobiose in an excellent manner by using the immobilized enzyme. When glucose-isomerase is used, fructose may be prepared from glucose. In addition, this immobilized, enzyme may also be used for the analytical determination of fructose in the presence of excess amounts of glucose. In the course of investigating the new immobilized enzymes, above all, there has been found that the bound enzymes, as compared to the free enzymes, have a higher resistance against thermal denaturation and even the optimum temperature is increased by a few degrees Centigrade. It has further been established that the pre-activated carrier is capable of undergoing an approximately quantitative reaction with the available protein in an aqueous solution and, therefore, the considerable excess of enzyme, otherwise necessary, can be avoided. According to the invention, due to the high active surface, especially favourable conditions of enzyme activity per unit weight of carrier are obtained.

Immobilized enzymes, processes for preparing same, and uses thereof according to the invention, are set forth in the following examples which are intended to illustrate, while not to be limitative to, the present invention. Comparative tests furnish evidence of the surprisingly good properties of the immobilized enzymes according to the invention.

EXAMPLE 1

(a) Introduction of Amino Groups at the Surface:

Spherical silica particles (30 g) having a diameter of from 30 to 70 μm, an apparent particle volume of 3 cm$^3$/g and a specific surface area of from 390 m$^2$/g and a chemical composition in excess of 99.5% of SiO$_2$, prepared according to Example 1 of the German Patent Application No. P 34 14 232 were washed five times with 100 ml of acetone and then stirred with 200 ml of a 5% solution of 3-aminopropyl triethoxysilane (APTS) in acetone overnight.

For comparison, pure quartz sand purified with concentrated nitric acid was also washed with acetone and reacted with APTS.

(b) Reaction of the Amino Groups with Glutaraldehyde:

Portions of 5 g of the carrier with the amino groups were reacted, each with 50 ml of a 2.5% solution of glutaraldehyde in a 0.1M potassium phosphate buffer (pH 7) while stirring for three hours. Then, the carriers were washed three times with 50 ml of phosphate buffer. In the form thus obtained, they may be directly subjected to the reaction with the enzymes.

(c) Reaction with Enzymes:

The reaction was carried out in 25 ml of two solutions containing 2.7 mg/ml and 5.4 mg/ml of protein, respectively, at 4° C. overnight. The results are summarized in the following Table 1.

TABLE 1

| Carrier | Amount of carrier (g) | mg of protein engaged | mg of protein in the supernatant | mg of protein bound per g of carrier |
|---|---|---|---|---|
| According to the invention | 5 | 67.5 | 1.35 | 13.2 |
| According to the invention | 5 | 135 | 66.5 | 13.8 |
| Sand | 5 | 67.5 | 60 | 1.5* |
| Sand | 5 | 135 | 132.5 | 0.5* |

*These values were determined by measuring the enzyme concentration of cellobiase. The data show that the carrier according to the invention is capable of binding a substantially higher amount of enzyme than quartz sand. The activity of cellobaise was determined in a solution of 8 mmol of p-nitrophenyl-β-D-glucopyranoside in 0.1 M sodium acetate buffer at pH 4.75. The p-nitrophenol product of the hydrolysis was directly measured by spectrophotometry at 420 nm in an alkaline medium.

In order to determine the binding strength between enzyme and carrier, the immobilized enzyme was incubated with the same substrate at 40° C. for 10 min. A sample of the supernatant was taken, and the amount of p-nitrophenol was measured in the sample and supernatant as a function of time. The result showed that no enzyme activating was present in the supernatant and that the immobilized enzyme continued to display its full activity.

In another experiment, the immobilized enzyme was consecutively treated with 4 samples of the substrate, and thereafter the respective residual activities were measured. The results showed that the activity remained constant.

The immobilized enzyme according to the invention was investigated in comparison with the non-bound enzyme with respect to the optimum temperature. To this end, samples were incubated in the presence of 8 mmol of p-nitrophenyl-β-D-glucopyranoside in a 0.1M sodium acetate buffer at pH 4.75 at a temperature of from 40° C. to 80° C. for 15 min. It was found that the optimum activity of the immobilized enzyme was higher by 7° C. than that of the free enzyme.

The thermal stability of the immobilized enzyme, in comparison to the non-bound enzyme, was investigated by heating both of them at 70° C. in an acetate buffer. Samples were taken at regular intervals and the activities thereof were measured. The results showed that the immobilized enzyme displayed 19% of its initial activity after one hour, whereas the unbound enzyme did not show any substantial activity after 20 minutes.

In addition, the immobilized enzyme was subjected to a comparative test with the unbound enzyme under production condition. To this end, it was reacted in the presence of a 10% solution of cellobiose in 0.1M sodium acetate buffer (pH 4.75). It was observed that after 60 hours reaction the unbound cellobiase did not show any more activity, whereas the immobilized enzyme bound to the carrier according to the invention still retained 95% of its initial activity. The immobilized enzyme bound to quartz sand as the carrier showed the same stability behavior as the unbound enzyme. After a reaction time of 118 hours, the natural enzyme had produced 1.6 g/l of glucose, while the immobilized enzyme according to the invention had produced 24.2 g/l of glucose. The enzyme bound to sand had produced 2.6 g/l of glucose.

Further comparative experiments were carried out using the same enzyme bound to a proved commercially available carrier based on polyacryloxiranes for enzymes (Eupergit C), the epoxy functions of which are able to undergo direct coupling with enzymes. It was established that the coupling of the enzyme to the new carrier, virtually independent of the protein concentration, amounted to 90 to 95% unless an excess of enzyme was added. Contrary thereto, there was found for the commercial product having the epoxy functions that the proportion of bound enzyme depends on the concentration of the enzyme. Up to 180 mg of protein/g of carrier can be bound to the carrier of the invention, while the commercial product is only able to bind 40 mg of enzyme/g of the carrier. It has further been determined that the activity of the enzyme bound to the commercial carrier is only 60% of the initial activity, whereas with the carrier according to the invention, essentially no decrease of the initial activity was observed.

EXAMPLE 2

The silica particles having been pre-treated and activated according to Example 1 were reacted with varying amounts of glucose-isomerase in a 0.1M sodium phosphate buffer at pH 7. To this end, 0.5 g of the carrier were reacted with 5 ml of enzyme solution, respectively, and mechanically stirred over night. The enzyme solution was contaminated by inactive protein of unknown origin. The amounts and results are listed in the following Table 2.

TABLE 2

| Test No. | Amount of carrier (g) | mg of protein | mg of protein in the supernatant | mg of protein bound to the carrier |
|---|---|---|---|---|
| 1 | 0.5 | 25 | 1.2 | 23.8 |
| 2 | 0.5 | 100 | 36 | 64 |
| 3 | 0.5 | 150 | 64 | 86 |

TABLE 2-continued

| Test No. | Amount of carrier (g) | mg of protein | mg of protein in the supernatant | mg of protein bound to the carrier |
| --- | --- | --- | --- | --- |
| 4 | 0.5 | 300 | 197 | 103 |

The activities of the supernatant and of the respective immobilized enzymes were determined, and the results are summarized in the following Table 3.

TABLE 3

| Test No. | Units employed (A) | Units in the supernatant (B) | Theoretically coupled units (A − B) | Units on the carrier (C) | Residual activity in % $\left(\dfrac{C}{A-B}\times 100\right)$ |
| --- | --- | --- | --- | --- | --- |
| 1 | 4.5 | 0 | 4.5 | 4.8 | 108 |
| 2 | 18 | 6.3 | 11.7 | 10.8 | 92 |
| 3 | 27 | 11.6 | 15.4 | 14.0 | 91 |
| 4 | 54 | 34.8 | 19.2 | 14.3 | 75 |

The units are defined as mmol of glucose formed/g of protein at 40° C. within 10 min.

The results reveal that the residual activity of the different samples is higher than 75%, although the carrier was also loaded with alien protein to a considerable extent. This shows that the protein is not deactivated by the new carrier but also thereafter remains accessible to the substrate, and that in spite of a high contamination of the enzyme with non-active protein, good results can be achieved. The further experiments were carried out with sample No. 3, since it represents the best compromise between activity and residual activity.

The activity of the immobilized enzyme was determined by measuring the amount of glucose formed in a substantial excess of fructose. Thereto, the glucose was oxidized to give gluconate by means of glucose-oxidase, and the hydrogen peroxide formed was destroyed by catalase. Oxygen was passed through the sample for 1 hour, and thereafter the gluconic acid formed was neutralized with sodium hydroxide solution. Then the samples were phosphorylated in the presence of ATP and were isomerized by the action of the enzyme glycose-isomerase. The glucose-6-phosphate having thus been formed is oxidized by glucose-6-phosphate dehydrogenase and is determined in the presence of NADP according to the uv method for glucose-fructose of Boehringer Mannheim.

What is claimed is:

1. An immobilized enzyme covalently bound to an inorganic carrier by an amino group through a bifunctional spacer, said carrier consisting of amorphous, approximately spherical silica particles obtained by the acidic hydrolysis of an approximately spherical synthetic calcium silicate having a particle size of from 20 to 120 μm, said silica particles having an average particle size of from 15 to 80 μm, an apparent particle volume of from 1.3 to 3 cm$^3$/g, and a specific surface area of from 250 to 800 m$^2$/g.

2. The immobilized enzyme of claim 1, wherein said carrier consists of silica particles treated with 3-aminopropyl triethoxysilane (APTS).

3. The immobilized enzyme of claim 2, wherein said carrier consists of silica particles treated with glutaraldehyde.

4. A process for the preparation of an immobilized enzyme covalently bound to an inorganic carrier by an amino group through a bifunctional spacer, comprising
    (a) providing amorphous, approximately spherical silica particles obtained by the acidic hydrolysis of an approximately spherical synthetic calcium silicate having a particle size of from 20 to 120 μm, said silica particles having an average particle size of from 15 to 80 μm, an apparent particle volume of from 1.3 to 3 cm$^3$/g, and a specific surface area of from 250 to 800 m$^2$/g; and
    (b) reacting the particles of step (a) with 3-aminopropyl triethoxysilane (APTS), glutaraldehyde, and an enzyme.

5. The process of claim 4, wherein said enzyme is cellobiase or glucose-isomerase.

6. A method for preparing glucose from cellobiose comprising
    providing immobilized cellobiase covalently bound to an inorganic carrier by an amino group through a bifunctional spacer, said carrier consisting of amorphous, approximately spherical silica particles obtained by the acidic hydrolysis of an approximately spherical synthetic calcium silicate having a particle size of from 20 to 120 μm, said silica particles having an average particle size of from 15 to 80 μm, an apparent particle volume of from 1.3 to 3 cm$^3$/g, and a specific surface area of from 250 to 800 m$^2$/g,
    subjecting said immobilized cellobiase to treatment to provide glucose, and
    recovering said glucose.

7. A method for preparing fructose from glucose comprising
    providing immobilized glucose-isomerase covalently bound to an inorganic carrier by an amino group through a bifunctional spacer, said carrier consisting of amorphous, approximately spherical silica particles obtained by the acidic hydrolysis of an approximately spherical synthetic calcium silicate having a particle size of from 20 to 120 μm, said silica particles having an average particle size of from 15 to 80 μm, an apparent particle volume of from 1.3 to 3 cm$^3$/g, and a specific surface area of from 250 to 800 m$^2$/g,
    subjecting said immobilized glucose-isomerase treatment to provide fructose, and
    recovering said fructose.

* * * * *